United States Patent [19]
Orr

[11] Patent Number: 5,853,375
[45] Date of Patent: Dec. 29, 1998

[54] GUIDE WIRE EXTENSION PEG AND HOLE WITH 90 DEGREE LATCH

[75] Inventor: Gregory C. Orr, Oceanside, Calif.

[73] Assignee: Medtronic, Inc., Minneapolis, Minn.

[21] Appl. No.: 968,915

[22] Filed: Nov. 6, 1997

Related U.S. Application Data

[63] Continuation of Ser. No. 564,026, Nov. 29, 1995, abandoned.

[51] Int. Cl.$^6$ ............................................. A61B 5/00
[52] U.S. Cl. ................................................. 600/585
[58] Field of Search ........................... 600/585; 403/224, 403/292–294, 298, 306, DIG. 4

[56] References Cited

U.S. PATENT DOCUMENTS

| | | | |
|---|---|---|---|
| Re. 34,466 | 12/1993 | Taylor et al. ............................ | 128/657 |
| 1,189,802 | 7/1916 | Eckert .................................... | 403/306 |
| 2,473,388 | 6/1949 | Rambo .................................... | 403/292 |
| 4,917,103 | 4/1990 | Gambale et al. ....................... | 128/772 |
| 4,922,923 | 5/1990 | Gambale et al. ....................... | 128/772 |
| 5,031,636 | 7/1991 | Gambale et al. ....................... | 128/772 |
| 5,109,867 | 5/1992 | Twyford, Jr. ........................... | 128/772 |
| 5,188,621 | 2/1993 | Samson .................................. | 604/283 |
| 5,195,535 | 3/1993 | Shank ..................................... | 128/772 |
| 5,197,486 | 3/1993 | Frassica ................................. | 128/772 |
| 5,234,002 | 8/1993 | Chan ...................................... | 128/772 |
| 5,269,759 | 12/1993 | Hernandez et al. .................... | 604/96 |
| 5,271,415 | 12/1993 | Foerster et al. ....................... | 128/772 |
| 5,395,389 | 3/1995 | Patel ...................................... | 606/194 |
| 5,399,590 | 3/1995 | Horrigan et al. ...................... | 128/772 |
| 5,513,650 | 5/1996 | Johansen ............................... | 128/772 |

FOREIGN PATENT DOCUMENTS

| | | | |
|---|---|---|---|
| 0416734 | 7/1990 | European Pat. Off. | ....... A61M 25/01 |
| 0415332 | 11/1995 | European Pat. Off. | ....... A61M 25/01 |

*Primary Examiner*—Max Hindenburg
*Attorney, Agent, or Firm*—Michael R. Shevlin; Dianne M.F. Plunkett; Harold R. Patton

[57] ABSTRACT

A guide wire extension assembly for angioplasty comprising a guide wire and an extension wire that utilize a peg and hole connection. The proximal end of the guide wire and the distal end of the extension wire have connector members attached that allow for mating the ends of the guide wire and extension wire together. In one embodiment the first connector member has a horizontal surface with a hole that is perpendicular to the horizontal surface. The second connector member has a horizontal surface with a peg extending upwardly from the horizontal surface, such that when the first connector member and the second connector member are joined, the peg and the hole fit together. In another embodiment, the first connection member and the second connection member are made from magnetic material so that when the peg is inserted in the hole, it is held in place by magnetic attraction. In another embodiment, the first connector member has a horizontal surface with a longitudinal slot that is perpendicular to the horizontal surface and extends through the first connection member. The second connector member has a horizontal surface with a peg extending upwardly from the horizontal surface with a latch on the end, the latch being dimensioned to be complementary to the slot, such that the latch fits through the slot and when the connection members are rotated away from each other, the latch locks the members together.

6 Claims, 3 Drawing Sheets

GUIDE WIRE EXTENSION PEG AND HOLE WITH 90 DEGREE LATCH

This application is a continuation of Ser. No. 08/564,026 filed Nov. 29, 1995, now abandoned.

FIELD OF THE INVENTION

This invention relates to guide wires used in angioplasty, and more particularly to the extension of the guide wire to facilitate the exchange of dilatation catheters.

BACKGROUND OF THE INVENTION

Dilatation balloon catheters are frequently used for the treatment of stenosis in the coronary arteries. This procedure, known as percutaneous transluminal coronary angioplasty (PCTA), was developed by Dr. Andreas Gruntzig. According to this procedure, a blockage in a coronary artery can be reduced by positioning a balloon dilatation catheter across the blockage and inflating the balloon, which causes stretching of the artery and pressing of the lesion into the artery wall to re-establish acceptable blood flow through the artery. The first marketable PCTA catheters for angioplasty were "fixed wire" catheters, in which a core or guide wire was fixed within the catheter to stiffen it so that it could be pushed into position in the vascular system. If a different catheter size was required, the fixed wire catheter had to be completely removed and a new one inserted. This is a tedious and time consuming process.

Dr. John Simpson and Dr. Edward Robert subsequently developed an "over-the-wire" catheter in which a guide wire was slidably placed within a lumen of the catheter. The guide wire lumen passed from the distal end of the catheter through the balloon to the proximal end of the catheter. This system provided reasonably easy placement of the catheter because the guide wire was inherently smaller and more flexible than the fixed wire system so one could more readily select the desired coronary artery and reach smaller branches. Once the guide wire was positioned beyond the stenosis, the catheter was then slid over the guide wire so that placement of the balloon spanned the stenosis and the balloon was then inflated. Once the catheter is inflated to dilate the stenosis, it is not uncommon for the physician to require use of a subsequent larger size of balloon to open the artery. There are different methods used to exchange the catheter and all of them have the same goal, to exchange the catheter without losing the position across the stenosis.

When performing the catheter exchange it is important to keep the guide wire in the same position so that the guide wire may be used to guide the next catheter to the stenosis. One method of exchange is to remove the initial guide wire and replace it with an exchange wire that is over double the length of the catheter. Once the exchange wire is in place, the catheter is slid over the exchange wire and the catheter is removed, then the next catheter is slid over the exchange wire to the stenosis.

Another method of exchanging the catheter is to use an extension wire. The extension wire is attached to the proximal end of the guide wire that is already in place. With the extension wire attached, the combination of the guide wire and extension wire is approximately the same length as an exchange wire. The advantage of this method is that the original guide wire that has already crossed the stenosis does not have to be disturbed during the catheter exchange.

There are different methods of attaching the extension wire to the guide wire. U.S. Pat. No. 4,917,103 to Gambale describes a male/female connection between the guide wire and extension wire that crimps the extension wire to the proximal end of the guide wire making a permanent connection. U.S. Pat. No. 5,197,486 to Frassica describes a connection where the proximal end of the guide wire has a reduced diameter male element that attaches to a female element at the distal end of the extension wire by using an interference fit. U.S. Pat. No. Re. 34,466 to Taylor describes another male/female connection between the guide wire and the extension wire.

There are other methods that add intermediate parts between the guide wire and extension wire that connects them together (see U.S. Pat. No. 5,188,621 to Samson, U.S. Pat. No. 5,271,415 to Foerster, U.S. Pat. No. 5,234,002 to Chan, U.S. Pat. No. 4,922,923 to Gambale, U.S. Pat. No. 5,031,636 to Gambale) or use retractable sleeves which enclose interlocking members of the guide wire and extension wire (see U.S. Pat. No. 5,109,867 to Twyford).

Another method of exchanging catheters is to trap the guide wire in or outside of the guiding catheter. The most common way to trap the guide wire is either using balloons or magnets. European Patent Application Publication number 0416734A1 to Coehlo, European Patent Application Publication number 0415332B1 to Keith, U.S. Pat. No. 5,395,389 to Patel, and U.S. Pat. No. 5,388,590 to Horrigan et al. have balloons with inflation lumens that are assembled in the guide catheter or are inserted into the guide catheter. When the balloons are inflated, the guide wire is trapped in place during a catheter exchange. U.S. Pat. No. 5,269,759 to Hernandez et al. uses a magnetic element to fix the guide wire longitudinally with respect to the guiding catheter.

There are problems associated with the aforementioned connections. Connections that use male/female friction to hold the guide wires together may disconnect if any torsional forces are used during the exchange. Connections that use crimping devices require special equipment, may be somewhat awkward to use and are not readily disconnectable. Connections with intermediate parts cannot connect the guide wires if those parts are lost or misplaced during a procedure. Connections using retractable sleeves may jam or stick with foreign material and not allow the connection. Connections using a trapping mechanism are complex and costly.

The object of the invention is to provide a new and improved guide wire extension that cures the problems that have been encountered by prior extension systems. This is accomplished by making a connection between the guide wire and the extension wire that makes it simple to attach the wires together, can transfer torsional forces between the wires without the fear of the wires coming apart or unscrewing and can be readily disconnected/reconnected when required.

SUMMARY OF THE INVENTION

Accordingly, the present invention is directed to a guide wire extension assembly comprising a guide wire and an extension wire that utilize a peg and hole connection between the guide wire and the extension wire when exchanging a balloon dilatation catheter, thus avoiding the need for a separate exchange wire. The proximal end of the guide wire and the distal end of the extension wire have connector members attached that allow for mating the ends of the guide wire and extension wire together. In one embodiment, the first connector member has a horizontal surface with a hole located near the center of the horizontal surface that is perpendicular to the horizontal surface and extends through the first connection member. The second connector member has a horizontal surface with a peg extending upwardly from the horizontal surface, the peg being dimensioned to be complementary to the hole such that when the first connector member and the second connector member are joined, the peg and the hole fit together and the combination of first and second connector members form a complete circle. In another embodiment, the first connection member and the second connection member are made from magnetic material so that when the peg is inserted in the hole, it is held in place by magnetic attraction. In another embodiment, the first connector member has a horizontal surface with a longitudinal slot located near the center of the horizontal surface that is perpendicular to the horizontal surface and extends through the first connection member. The second connector member has a horizontal surface with a peg extending upwardly from the horizontal surface with a latch on the end, the latch being dimensioned to be complementary to the slot and oriented perpendicular to the longitudinal axis, such that when the first connector member and the second connector member are at 90 degrees to each other, the latch fits through the slot and when the connection members are rotated away from each other, the latch locks the members together.

BRIEF DESCRIPTION OF THE DRAWINGS

The foregoing and other features of the present invention will be best appreciated with reference to the following detailed description of a specific embodiment of the invention, when read in conjunction with the accompanying drawings.

DETAILED DESCRIPTION OF THE PREFERRED EMBODIMENTS

The present invention is directed to a guide wire extension system 10 utilizing a peg and hole connection between the guide wire 15 and the extension wire 20, thus avoiding the need for a separate exchange length wire when exchanging a balloon dilatation catheter. The proximal end of the guide wire 15 and the distal end of the extension wire 20 are joined together create a guide wire extension system 10 utilizing the peg and hole connection. The peg, when inserted in the hole, can be held in place by a variety of methods including friction, magnetic attraction or mechanical locking. The connection between the guide wire and the extension wire makes it simple to attach the wires together, transfers torsional forces between the wires without the fear of the wires coming apart or unscrewing and is readily disconnected/reconnected when required. While the following describes the peg to be on the end of guide wire 15 and hole to be on the end of extension 20, it could also be the other way around.

Figure 1:
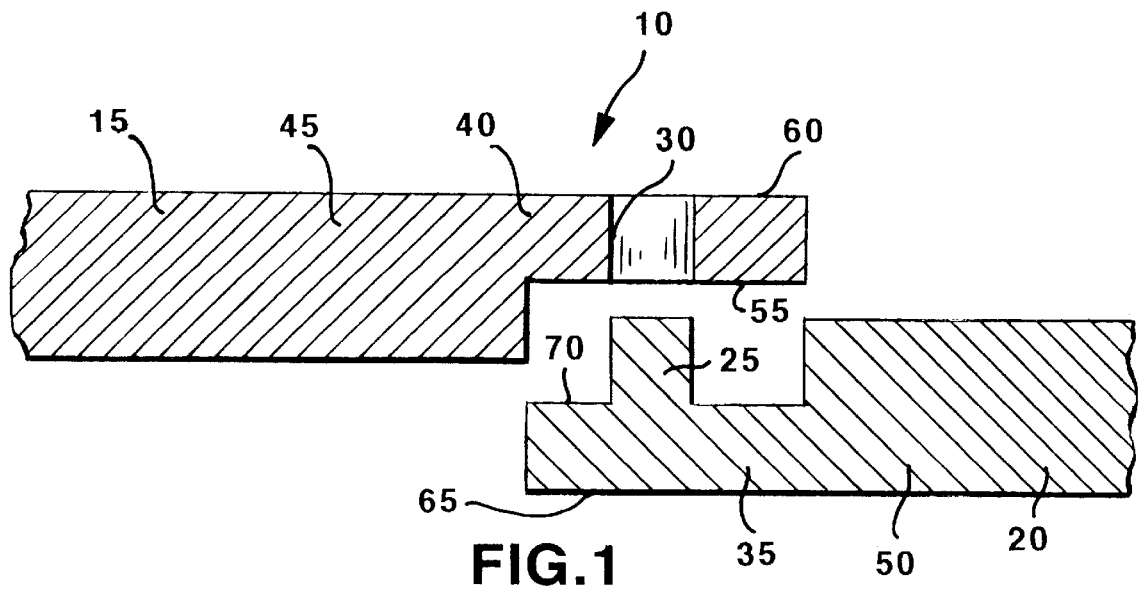
FIG. 1 is a cross-sectional view of the proximal end of the guide wire and the distal end of the extension wire showing the connection features of the present invention.
Figure 2:
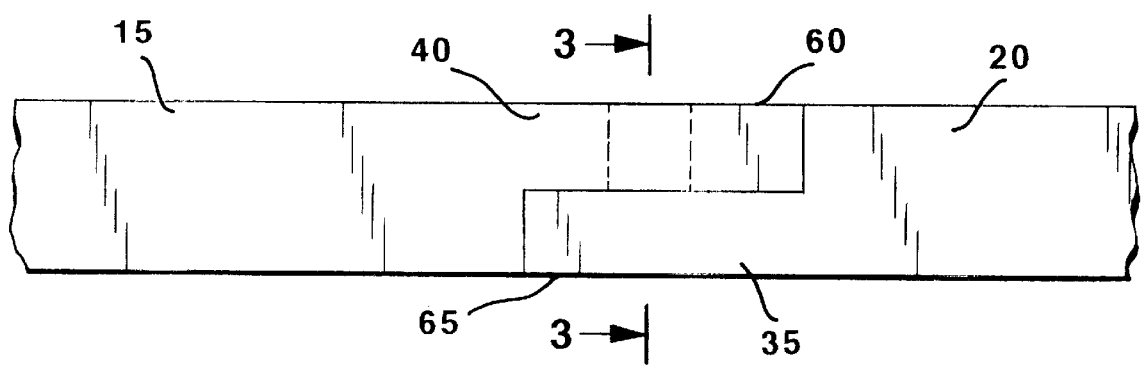
FIG. 2 is a view showing the assembled joint connection of the guide wire and extension wire assembly of FIG. 1.
Figure 3:
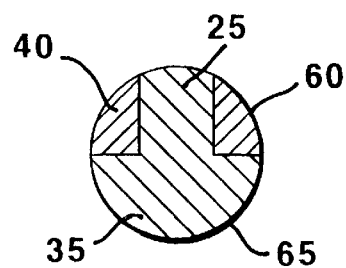
FIG. 3 is a transverse cross-sectional view taken at 3—3 of FIG. 2 showing the guide wire and extension wire assembly assembled.
Figure 4:
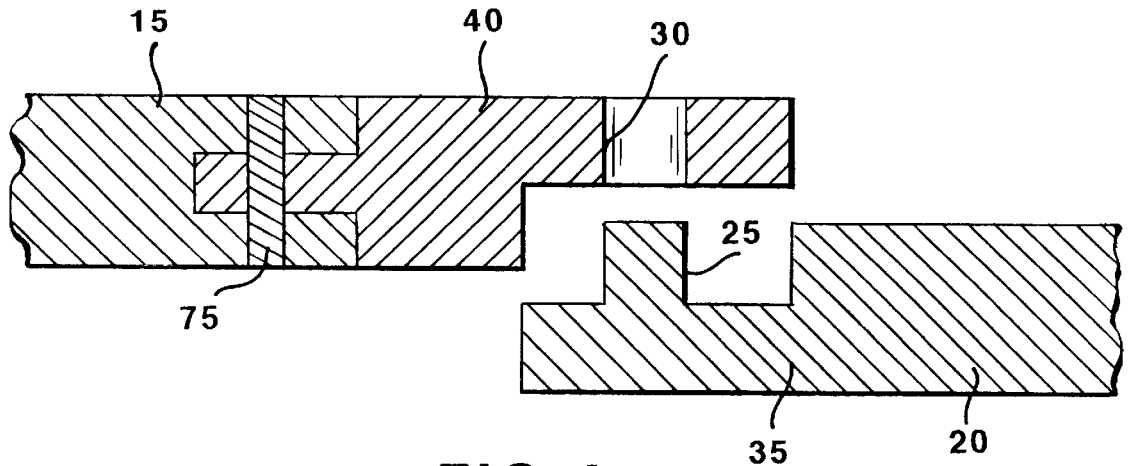
FIG. 4 is an additional cross-section view of the proximal end of the guide wire and the distal end of the extension wire showing an alternate configuration for guide wire and extension wire assembly of the present invention.
Figure 5:
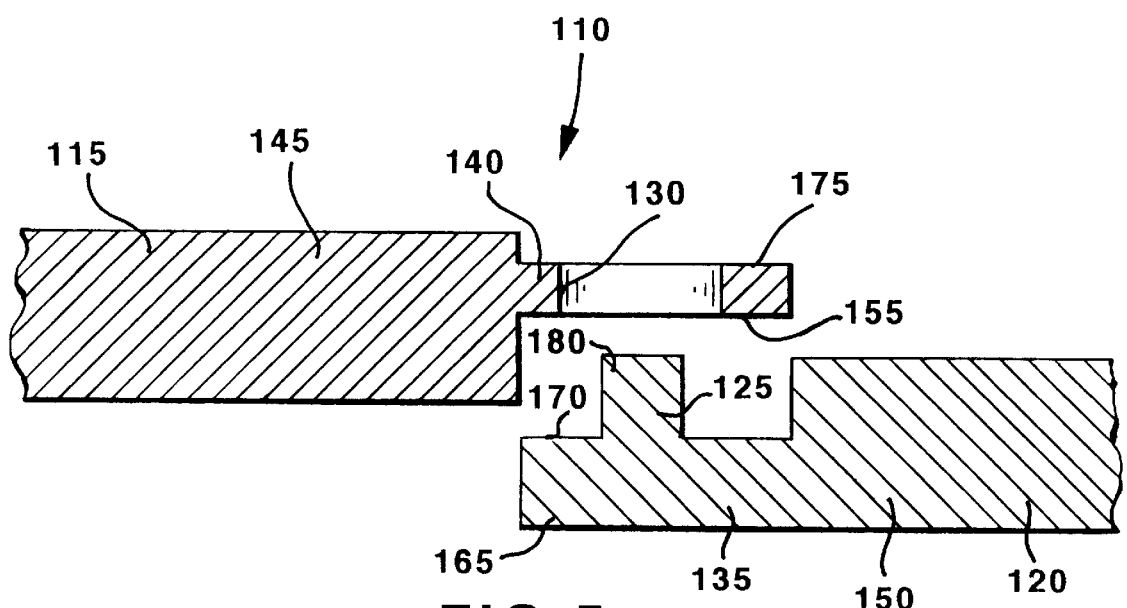
FIG. 5 is an additional cross-section view of the proximal end of the guide wire and the distal end of the extension wire showing the 90 degree latch configuration for guide wire and extension wire assembly of the present invention.
Figure 6:
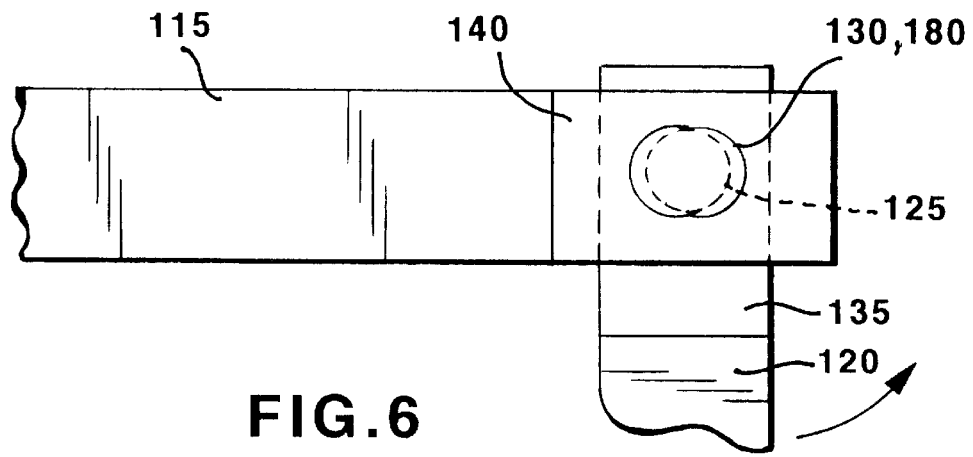
FIG. 6 is a top view of FIG. 5 showing the proximal end of the guide wire and the distal end of the extension wire being joined together.
Figure 7:
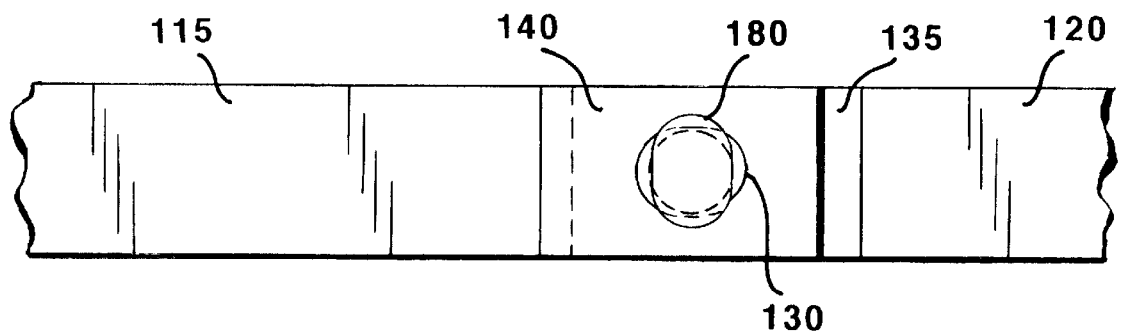
FIG. 7 is a view showing the assembled joint connection of the guide wire and extension wire assembly of FIG. 5.

FIGS. 1–4 show the first embodiment of the present invention of a guide wire extension system 10, which includes guide wire 15 with connection member 40 with hole 30 at its proximal end 45 and an extension wire 20 with connection member 35 with peg 25 at its distal end 50. Guide wire 15 is made of any guide wire construction modified at its proximal end 45 with connection member 40. Standard guide wires for angioplasty are constructed of metal (stainless steel, nitinol, etc.) and have diameters of ranging from 0.010" to 0.018". The exact construction of guide wire 15 (other than the proximal end 45) is not critical to the invention and will not be described in any detail. Connection member 40 is located at the proximal end 45 of guide wire 15, connection member 40 may either be constructed as part of guide wire 15 or attached to proximal end 45 by bonding, soldering or welding. FIG. 4 shows an alternate configuration in which connection member 40 is mechanically attached with the proximal end of guide wire 15 using pin 75 and connection member 40 is constructed from a material that is magnetized or is magnetic, such as alnico, cunife or rare earth alloys, so that when connection member 40 is joined with connection member 35, they are held together with magnetic attraction. Connection member 40 comprises an upwardly curved outer surface 60 and a flat mating surface 55 that runs through the horizontal axis of guide wire 15. The curved outer surface 60 has a radius the same as guide wire 15 (see FIG. 3) and the width of surface 55 is the same as the diameter of guide wire 15. At the center of surface 55 is hole 30, hole 30 extends through connection member 40 perpendicular to surface 55 and is dimensioned to receive peg 25.

Extension wire 20 is generally formed from a elongated, constant diameter wire modified at its distal end 50 with connection member 35. Connection member 35 may either be constructed as part of extension wire 20 or attached to distal end 50 by bonding, soldering or welding. FIG. 4 shows an alternate configuration in which connection member 35 is constructed from a material that is magnetized or is magnetic, such as alnico, cunife or rare earth alloy, so that when connection member 35 is joined with connection member 40, they are held together with magnetic attraction. Connection member 35 comprises a downwardly curved outer surface 65 and a flat mating surface 70 that runs through the horizontal axis of extension wire 20 and mates with surface 55 of connection member 40. The curved outer surface 65 has the same radius as extension wire 20 (see FIG. 3) and the width of surface 70 is the same as the diameter of extension wire 20. At the center of surface 70 is peg 25, peg 25 extends upwardly from surface 70 and has a height equal to the radius of guide wire 15 (between 0.005" and 0.009") and a diameter equal to one half the diameter of guide wire 15 (between 0.005" and 0.009").

The guide wire 15 is connected to the extension wire 20 by mating the proximal end 45 of the guide wire 15 and the distal end 50 of the extension wire 20 so that peg 25 of connection member 35 is inserted into hole 30 of connection member 40 connecting extension wire 20 to guide wire 15, as shown in FIG. 2. The length of connection member 40 can vary between 0.050 to 0.500 inches. FIG. 3 shows a cross-sectional view of the connection between peg 25 and hole 30. This connection will hold guide wire 15 and extension wire 20 together during the catheter exchange and resist disengagement but can be readily disengaged after the catheter exchange has been made. Preferably no more than a one pound pull should be necessary for disengagement.

FIGS. 5–8 show a second embodiment of the present invention utilizing a 90 degree latch connection of guide wire extension system 100, which includes guide wire 115 with connection member 140 at its proximal end 145 and an extension wire 120 with connection member 135 at its distal end 150. Guide wire 115 is made of any guide wire construction modified at its proximal end 145 with connection member 140. Standard guide wires for angioplasty are constructed of metal (stainless steel, nitinol, etc.) and have diameters of ranging from 0.010" to 0.018". The exact construction of guide wire 115 (other than the proximal end 145) is not critical to the invention and will not be described in any detail. Connection member 140 is located at the proximal end 145 of guide wire 115, connection member 140 may either be constructed as part of guide wire 115 or attached to proximal end 145 by bonding, soldering or welding. Connection member 140 comprises flat mating surface 155 that runs through the horizontal axis of guide wire 115, an upper surface 175 parallel to surface 155, both surfaces connected by an upwardly curved outer surface 160. The curved outer surface 160 has a radius the same as guide wire 115 (see FIG. 8) and the width of surface 155 is the same as the diameter of guide wire 115 and the distance between surface 155 and surface 175 is approximately the same as the length of peg 125. Near the center of surface 155 is slot 130. Slot 130 is oriented along the longitudinal axis of guide wire 115 extends through connection member 140 perpendicular to surface 155 and is dimensioned to receive latch 180.

Extension wire 120 is generally formed from an elongated, constant diameter wire modified at its distal end 150 with connection member 135. Connection member 135 may either be constructed as part of extension wire 120 or attached to distal end 150 by bonding, soldering or welding. Connection member 135 comprises a downwardly curved outer surface 165 and a flat mating surface 170 that runs through the horizontal axis of extension wire 120 and mates with surface 155 of connection member 140. The curved outer surface 165 has the same radius as extension wire 20 (see FIG. 8) and the width of surface 170 is the same as the diameter of extension wire 120. Near the center of surface 170 is peg 125. Peg 125 extends upwardly from surface 170 and has a diameter equal to one half the diameter of guide wire 115 (between 0.005" and 0.009")and a length equal to the thickness of connection member 140. The other end of Peg 125 is attached to Latch 180. Latch 180 has the same shape as slot 130 and can be slid through slot 130 and is oriented perpendicular to the longitudinal axis of extension wire 120.

Figure 8:
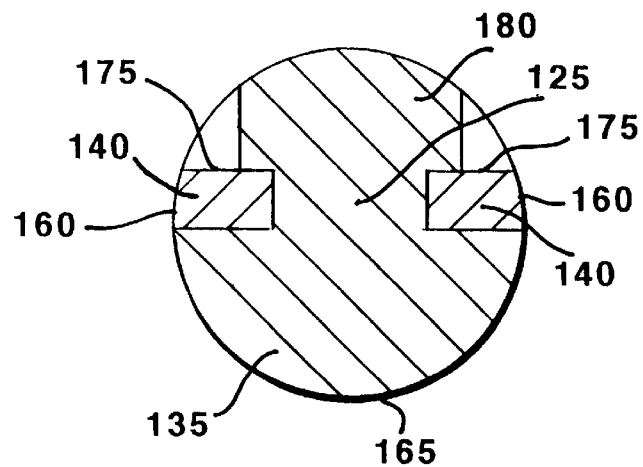
FIG. 8 is a enlarged transverse cross-sectional view similar to FIG. 3 showing the 90 degree latch configuration between the guide wire and extension wire in the locked position.

The guide wire 115 is connected to the extension wire 120 by mating the proximal end 145 of the guide wire 115 and the distal end 150 of the extension wire 120. First the distal end 150 is brought near the proximal end 145 of guide wire 115 at a 90 degree angle. Latch 180 is then slid through slot 130 until surface 155 of connection member 140 meets surface 170 of connection member 135. At this point, latch 180 is completely through slot 130 (see FIG. 6). The extension wire 120 is then rotated 90 degrees away from guide wire 115 and locks the wires together forming guide wire extension system 110 (see FIG. 7). The length of connection member 140 can vary between 0.050 to 0.500 inches. FIG. 8 shows a cross-sectional view of the connection between peg 125, latch 180 and slot 130. The connection with peg 125 inserted into slot 130 and locked in place with latch 180 will hold guide wire 115 and extension wire 120 together during the catheter exchange and resist disengagement but can be readily disengaged after the catheter exchange has been made by simply rotating extension wire 90 degrees and disengaging latch 180 from slot 130.

The proximal end (45, 145) of guide wire (15, 115) is adapted to engage and secure the distal end (50, 150) of extension wire (15, 115) so that rotation of extension wire (20, 120) causes rotation of guide wire (15, 115) through the connection. Extension wire (20, 120) is sufficiently long so that when the guide wire (15, 115) and extension wire (20, 120) are connected together, the combination has an overall length suitable for exchanging catheters without removing guide wire (15, 115) from the patient's vascular system. The length of guide wire (15, 115) is approximately 175–195 cm and the length of extension wire (20, 120) is approximately 125 cm. The connection between the two wires provides a smooth, substantially continuous outer diameter between the guide wire (15, 115) and extension wire (20, 120). The smooth, continuous outer diameter of the connection prevents snagging of the catheter during the exchange.

In use, guide wire (15, 115) is introduced into the patient with a balloon dilatation catheter in the patient's femoral artery. The guide wire (15, 115) is advanced to the selected coronary artery and across the stenosis. Once in place, guide wire (15, 115) is held in place as the balloon dilatation catheter is advanced along guide wire (15, 115) until the inflatable balloon spans the stenosis. The balloon is then inflated to dilate the stenosis. While in the patient, the only part of the guide wire (15, 115) that is exposed is the proximal end (45, 145) with connection member (40, 140). To exchange the catheter, the balloon is deflated, the distal end (50, 150) of extension wire (20, 120) with connection member (35, 135) is then attached to connection member (40, 140) at the proximal end (45, 145) of guide wire (15, 115) for positive engagement. Once connected, guide wire (15, 115) and extension wire (20, 120) will act as one unit and may be twisted and rotated. While holding the extension wire (20, 120), the balloon catheter is removed by sliding it off over the extension wire (20, 120). The new catheter is then slid on over the extension wire (20, 120) and guide wire (15, 115) until its balloon reaches the stenosis. Extension wire (20, 120) may then be disengaged from guide wire (15, 115).

Although a particular embodiment of the invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention. For example, guide wire 15 and/or extension wire 20 could be made of different metals or plastic and the diameter of each could vary and the shapes and dimensions of both peg 25 and hole 30 can have many configurations. This invention does not have to be limited to angioplasty, it could also be used in angiography and the invention could be introduced using the radial or brachial approach, not just the femoral artery.

| No. | Component |
| --- | --- |
| 10 | Guide Wire Extension System |
| 15 | Guide Wire |
| 20 | Extension Wire |
| 25 | Peg |
| 30 | Hole |
| 35 | Connection Member (on extension wire 20) |
| 40 | Connection Member (on guide wire 15) |
| 45 | Guide Wire - Proximal End |
| 50 | Extension Wire - Distal End |
| 55 | Flat Mating Surface (on connection member 40) |
| 60 | Curved Outer Surface (on connection member 40) |
| 65 | Curved Outer Surface (on connection member 35) |
| 70 | Flat Mating Surface (on connection member 35) |
| 75 | Pin |
| 110 | Guide Wire Extension System |
| 115 | Guide Wire |
| 120 | Extension Wire |
| 125 | Peg |
| 130 | Slot |
| 135 | Connection Member (on extension wire 120) |
| 140 | Connection Member (on guide wire 115) |
| 145 | Guide Wire - Proximal End |
| 150 | Extension Wire - Distal End |
| 155 | Flat Mating Surface (on connection member 140) |
| 160 | Curved Outer Surface (connecting surfaces 155 and 175) |
| 165 | Curved Outer Surface (on connection member 135) |
| 170 | Flat Mating Surface (on connection member 135) |
| 175 | Latching Surface (parallel to surface 155) |
| 180 | Latch |

What is claimed is:

1. A guide wire extension assembly for angioplasty including a guide wire and an extension wire to facilitate exchanging a balloon dilatation catheter comprising:

(a) a guide wire having a proximal end, a distal end and a radius;

(b) an extension wire having a proximal end, distal end and a radius;

(c) a first connector member and a second connector member;

(d) the first connector member being mated to one end of the guide wire comprising at least one horizontal surface extending along or parallel to the horizontal axis of the first connector member from the mated end to the opposed end, a longitudinally upwardly curved outer surface connecting the longitudinal sides of the horizontal surface or surfaces and extending from the mated end to the opposed end having the same radius as the guide wire and a first connection means located near the center of the horizontal surface; and (e) the second connector member being mated to one end of the extension wire, the second connector member comprising a horizontal surface extending along the horizontal axis from the mated end to the opposed end, a longitudinally downwardly curved outer surface connecting the longitudinal sides of the horizontal surface and extending from the mated end to the opposed end having the same radius as the extension wire and a second connection means located near the center of the horizontal surface that is complementary and connectable with the first connection means such that when the first connection means and the second connection means are vertically connected the guide wire and extension wire are joined together.

2. The guide wire extension assembly of claim 1 wherein the guide wire and extension wire are made of stainless steel.

3. The guide wire extension assembly of claim 1 wherein the first and second connection members are made of magnetic material to assist in holding the second connection means in the hole.

4. The guide wire extension assembly of claim 1 wherein the first connection means is a hole located near the center of the horizontal surface that is perpendicular to the horizontal surface and extends through the first connection member and the second connection means is a peg located near the center of the horizontal surface of the second connector member and the peg is perpendicular to the horizontal surface and extending upwardly from the horizontal surface, the peg being dimensioned to be complementary to the hole such that when the first connector member and the second connector member are joined, the peg and the hole fit together.

5. The guide wire extension assembly of claim 1 wherein the mating of the first connector to the guide wire is a removable connection.

6. The guide wire extension assembly of claim 1 wherein the first connection member has a second horizontal surface being offset above and parallel to the horizontal surface extending along the horizontal axis and the first connection means is a slot located near the center of the horizontal surfaces, the slot being longitudinally oriented and having a longer length than width, the slot extending perpendicularly through the first connection member and the second connection means is a peg having a shape located near the center of the horizontal surface of the second connection member, the peg extending perpendicularly upward from the horizontal surface, the peg having a first end and a second end, the peg being dimensioned to rotatably fit the narrow width of the slot with a height equal to the thickness of the first connector member, the first end of the peg being connected to the horizontal surface, the second end being connected to a latch, the latch having a thickness and being parallel to the horizontal surface, the latch dimensioned to be complimentary to the slot with the longer length of the latch being oriented perpendicular to the longitudinal axis and such that when the first connector member and the second connector member are at a 90 degree angle to each other, the latch fits the slot and once through the slot, the connection members are rotated 90 degrees locking the first and second connector members together.

* * * * *